United States Patent [19]

Cataldo et al.

[11] Patent Number: 5,856,271
[45] Date of Patent: Jan. 5, 1999

[54] METHOD OF MAKING CONTROLLED RELEASED DEVICES

[75] Inventors: Dominic C. Cataldo, Kennewick; Peter Van Voris, Richland, both of Wash.

[73] Assignee: Battelle Memorial Institute, Richland, Wash.

[21] Appl. No.: 699,464

[22] Filed: Aug. 19, 1996

Related U.S. Application Data

[63] Continuation-in-part of Ser. No. 482,300, Jun. 7, 1995.

[51] Int. Cl.⁶ ................................................ A01N 25/10
[52] U.S. Cl. ................ 504/116; 424/409; 424/DIG. 11; 514/953; 514/964
[58] Field of Search ............................. 504/116; 424/409, 424/DIG. 11; 514/953, 964

[56] References Cited

U.S. PATENT DOCUMENTS

| | | | |
|---|---|---|---|
| 2,970,404 | 2/1961 | Beaufils et al. | 47/57.5 |
| 3,502,458 | 3/1970 | Schenk | 71/64 |
| 3,592,792 | 7/1971 | Newland et al. | 260/41 |
| 3,639,583 | 2/1972 | Cardarelli et al. | 424/125 |
| 3,671,548 | 6/1972 | Itaya et al. | 549/79 |
| 3,705,938 | 12/1972 | Hyman et al. | 424/19 |
| 3,716,560 | 2/1973 | Taya et al. | 549/471 |
| 3,759,941 | 9/1973 | Sampei et al. | 548/117 |
| 3,835,176 | 9/1974 | Matsuo et al. | 558/407 |
| 3,835,220 | 9/1974 | Matsui et al. | 424/40 |
| 3,846,500 | 11/1974 | Kitamura et al. | 568/660 |
| 3,851,053 | 11/1974 | Cardarelli | 424/78 |
| 3,864,388 | 2/1975 | Kitamura et al. | 560/60 |
| 3,867,542 | 2/1975 | Ueda et al. | 514/461 |
| 3,876,681 | 4/1975 | Okuno et al. | 560/124 |
| 3,891,423 | 6/1975 | Stanley et al. | 71/86 |
| 3,899,586 | 8/1975 | Okuno et al. | 514/417 |
| 3,906,089 | 9/1975 | Okuno et al. | 424/45 |
| 3,954,814 | 5/1976 | Mizutani et al. | 549/499 |
| 3,966,963 | 6/1976 | Okuno et al. | 514/531 |
| 3,970,703 | 7/1976 | Kitamura et al. | 568/662 |
| 3,981,903 | 9/1976 | Hirano et al. | 560/124 |
| 3,998,868 | 12/1976 | Mitzutani et al. | 560/124 |
| 4,003,945 | 1/1977 | Kitamura et al. | 560/124 |
| 4,037,352 | 7/1977 | Hennart et al. | 43/129 |
| 4,063,919 | 12/1977 | Grano, Jr. | 71/11 |
| 4,065,555 | 12/1977 | Potter | 424/83 |
| 4,118,505 | 10/1978 | Kitamura et al. | 514/438 |
| 4,176,189 | 11/1979 | Itaya et al. | 514/389 |
| 4,212,879 | 7/1980 | Ohsumi et al. | 514/427 |
| 4,229,469 | 10/1980 | Mizutani et al. | 514/519 |
| 4,237,113 | 12/1980 | Cardarelli | 424/78 |
| 4,263,463 | 4/1981 | Kitamura et al. | 568/873 |
| 4,269,626 | 5/1981 | Gorke et al. | 106/18.32 |
| 4,279,924 | 7/1981 | Suzuki et al. | 514/521 |
| 4,293,504 | 10/1981 | Suzuki et al. | 558/354 |
| 4,320,113 | 3/1982 | Kydonieus | 424/27 |
| 4,327,109 | 4/1982 | Mizutani et al. | 514/443 |
| 4,336,194 | 6/1982 | Ohsumi et al. | 548/562 |
| 4,344,250 | 8/1982 | Fahlstrom | 47/57.5 |
| 4,348,218 | 9/1982 | Bond, Jr. | 71/1 |
| 4,350,678 | 9/1982 | Palvarini et al. | 424/27 |
| 4,376,785 | 3/1983 | Matsuo et al. | 514/521 |
| 4,400,374 | 8/1983 | Cardarelli | 424/78 |
| 4,496,586 | 1/1985 | Matsui et al. | 514/531 |
| 4,503,071 | 3/1985 | Hirano et al. | 514/521 |
| 4,576,801 | 3/1986 | Parry et al. | 427/288 |
| 4,680,328 | 7/1987 | Dohrer et al. | 524/137 |
| 4,747,902 | 5/1988 | Saitoh | 156/244.11 |
| 4,767,812 | 8/1988 | Chapin et al. | 524/144 |
| 4,808,454 | 2/1989 | Saitoh | 428/40.6 |
| 4,842,860 | 6/1989 | Suguira et al. | 424/403 |
| 4,886,656 | 12/1989 | Obayashi et al. | 514/144 |
| 5,104,659 | 4/1992 | Fishbein et al. | 424/411 |
| 5,292,504 | 3/1994 | Cardin et al. | 514/65 |
| 5,296,227 | 3/1994 | Norval et al. | 424/411 |
| 5,439,924 | 8/1995 | Mills | 514/345 |

FOREIGN PATENT DOCUMENTS

| | | |
|---|---|---|
| AU 91/82443 A | 8/1991 | Australia . |
| B-82443/91 | 2/1992 | Australia ............ A01N 25/10 |
| 95/13886 A1 | 8/1995 | Australia . |
| 0 286 009 A2 | 10/1988 | European Pat. Off. ........ B27K 3/50 |
| 77 72802 | 6/1977 | Japan ................ B27K 3/34 |
| 86/1133 | 2/1986 | South Africa . |
| WO 84/02447 | 7/1984 | WIPO ............ A01N 25/34 |
| WO 95/18532 | 7/1995 | WIPO ............ A01N 25/34 |

OTHER PUBLICATIONS

Burton, et al., "A Controlled–Release Herbicide Device for Multiple–Year Control of Roots at Waste Burial Sites," *J. of Controlled Release* (1985), 8 pages.

Chang, et al., "Control of Ant Damage to Polyethylene Tubes Used in Drip Irrigation Systems in Hawaiian Sugarcane Fields," *International Society of Sugar Cane Technologists* (02/01–11/80), p. 1686–1692.

Chen, et al., "Approaches to the Improvement of Biological Resistance of Wood through Controlled Release Technology," *Proceedings of the 13th Int'l Symposium on Controlled Release of Bioactive Materials* (08/3–6/86), pp. 75–76.

Kumar, et al., "The effect . . . treated wood," *J. Timber Dev . . . India* (1977), 23(3), pp. 9–13.

*Primary Examiner*—S. Mark Clardy
*Attorney, Agent, or Firm*—Paul W. Zimmerman

[57] ABSTRACT

The invention is a method of making a controlled release device that is free of defects. According to one aspect of the present invention, a method has the steps of first combining an active chemical with a dried carrier into a bound friable mixture followed by combining the bound friable mixture with a polymer preform prior to forming a device. According to another aspect of the present invention, a method has the steps of heating and mixing a casting urethane with an active chemical into a first solution, heating and mixing a trialkanolamine with a soft segment cross-linker into a second solution, and mixing the two solutions. A further aspect of the present invention is a composition of a casting urethane.

47 Claims, 3 Drawing Sheets

METHOD OF MAKING CONTROLLED RELEASED DEVICES

CROSS REFERENCE TO RELATED APPLICATIONS

This application is a Continuation-In-Part of application Ser. No. 08/482,300 filed Jun. 7, 1995.

FIELD OF THE INVENTION

The present invention relates generally to a method for making controlled release devices. More specifically, the invention is a method of combining an active chemical into a polymer, or combining an active chemical into a polymer with a carrier, for control of plants, pests, odor, medicine or other controlled release purpose. In this application, pests include but are not limited to arachnids, millipedes, insects, particularly crawling insects, winged insects, and boring insects. Crawling insects include but are not limited to roaches, ants, silverfish, and earwigs. Winged insects include but are not limited to flies, gnats, mosquitos, mantises, grasshoppers, and wasps. Boring insects include but are not limited to root borers, termites, and boring beetles.

BACKGROUND OF THE INVENTION

Controlled release devices are used to control plants, and pests. Most controlled release devices are a combination of an active chemical, for example a pesticide, with a polymer, for example polyethylene. Other controlled release devices include a carrier, for example carbon black.

South African patent 86133 lodged 14 FEB. 1986, entitled DRIP IRRIGATION SYSTEMS describes a "master batch" used for making drip emitters that prevent root intrusion. The master batch is described as a blend of 58 parts by mass of polyethylene powder with 18 parts by mass carbon black and heated to 70° C. Separately, 24 parts by mass of trifluralin are heated to melt the trifluralin and the melted trifluralin is slowly added to the polymer/carbon black mixture to make a friable mixture having from about 20–33 wt % trifluralin. The friable master batch is further combined with 90% by mass synthetic resin making a master batch combination achieving about 1–5 wt % trifluralin. The master batch combination is then injection molded. This master batch process is particularly aimed at high tolerance devices wherein a dilution of the trifluralin within the master batch is required (i.e., 30 wt % to 5 wt % trifluralin).

However, it has been found that this master batch combination has problems during injection molding. Specifically, as the master batch combination passes through the injection molder, the temperature of the master batch increases thereby increasing the vapor pressure of the trifluralin so that vaporized trifluralin issues forth from the master batch creating bubbles and voids greater than about 10% by volume in a size range from 0.05 mm to 0.5 mm in the injection molded product. The problem of increased vapor pressure of the trifluralin was partially overcome by increasing mixing time of the master batch combination prior to injection molding. However, the increased mixing time did not fully eliminate the bubbles and voids. In addition to production problems, the bubbles and voids caused a reduction in longevity of the product. When voids and bubbles were present, the active chemical was-released faster than desired, and the release rate was less predictable.

Thus, there is a need for a method of making a controlled release device that is moldable without flaws, bubbles and voids, and specifically there is a need for a method of making a controlled release device that is injection moldable.

SUMMARY OF THE INVENTION

The invention is a method of making a controlled release device that has fewer bubbles and voids. According to one aspect of the present invention, a method has the steps of first combining an active chemical with a dried carrier into a bound friable mixture followed by combining the bound friable mixture with a polymer preform making a formable mixture prior to forming a device. A bound friable mixture is one in which the active chemical is bound by the carrier prior to exposure to the polymer preform in distinction from the prior art wherein the active chemical (trifluralin) was added to a polymer/carrier mixture wherein a portion of active chemical (trifluralin) was free to coat the surface of polymer particles or mix with a monomer liquid without contacting a carrier particle while a second portion of the active chemical (trifluralin) became bound to the carrier. The term "bound" includes either sorption beyond a surface to an interior of a carrier particle volume, coating the carrier particle surface, or both. According to the present invention, a portion of the active chemical may "weep" from the carrier onto or into the polymer preform so that the "weep" portion of the active chemical is not in contact or bound by the carrier particle, but the amount of active chemical subject to "weeping" is substantially less than the amount of active chemical coating or mixing in the friable mixture of the prior art as observed by fewer bubbles and voids.

According to another aspect of the present invention, a microsponge of polymer holds active chemical permitting the active chemical to wet the surface of the microsponge without dripping from or crystallizing on the surface so that as an insect contacts the surface, active chemical is removed from the surface onto the insect. The active chemical from within the microsponge replenishes the location(s) on the surface where active chemical has been removed.

The microsponge is made according to a method having the steps of heating and mixing an amine curable elastomer pre-polymer (casting urethane) with an active chemical into a first solution, heating and mixing an amine (trialkanolamine) with a soft segment cross-linker into a second solution, and mixing the two solutions. A further aspect of the present invention is a composition of a casting urethane.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

DESCRIPTION OF THE PREFERRED EMBODIMENT(S)

FIRST ASPECT

According to a first aspect of the present invention, a method of making a controlled release device having a polymer, a carrier, and an active chemical, has the steps of:

(a) insuring that the active chemical is blendable with the carrier;

(b) removing moisture from the carrier;

(c) blending the active chemical with the dried carrier into a bound friable mixture;

(d) adding the bound friable mixture into an amount of a polymer preform and forming a formable mixture;

(e) forming the formable mixture into the controlled release device.

It is critical to the present invention that little or no polymer preform be present upon initial blending of the active chemical with the dried carrier to avoid development of flaws during forming.

The carrier is preferably a carbon product, for example activated carbon, carbon black, graphite or combinations thereof. Alternatively, the carrier may be an alumina, silicon-alumina, apatite or combination thereof. Apatite (calcium phosphate) is preferred for use with active chemicals which have lower absorption into other carriers, for example carbon black.

The polymer preform may be a polymer powder or a pre-polymer. The polymer preform may be any polymer, including but not limited to polyester, polypropylene, polyethylene, aromatic (e.g. styrene copolymer), specifically Kraton (a styrene block copolymer), polyurethane (e.g. Pellethane, Aromatic 80A, Aliphatic PS-49), aliphatic, polyolefins (e.g. polyisoprene, polybutadiene), a thermoset including but not limited to casting urethanes (e.g. solithane), polyolefins, epoxies, and combinations thereof, for example carboxylated latex with epoxy resin (Shell Hycar).

In a preferred method, the step of adding involves (i) dispersing the bound friable mixture into an amount of the polymer powder wherein the amount of the polymer powder is greater than the amount of bound friable mixture by weight thereby making a premixture; and (ii) mixing the premixture with an additional amount of the polymer powder, wherein the additional amount is greater than the amount of the premixture by weight thereby making the formable mixture.

Alternatively, the step of adding may involve (i) selecting an amine curable pre-polymer;

(ii) heating and mixing the pre-polymer with the active chemical and the bound friable mixture making a first solution;

(iii) heating and mixing a trialkanolamine with a soft segment cross-linker making a second solution; and (iv) pouring the second solution together with the first solution into a combined solution and continuing heating while mixing said combined solution into a castable mixture. In this alternative embodiment, the forming step is by casting.

A controlled release device made in accordance with this first aspect of the present invention is estimated to have an active life from 2 months to over 60 years. Shorter life products (2 months to 2 years) are typically made from amine curable pre-polymer, whereas longer life products (2 years to over 60 years) are generally made from a thermoplastic, preferably with a carrier.

The active chemical is any chemical that is desired to be slowly released from the polymer, including but not limited to pesticides, perfumes, pheromones, air fresheners, drugs, and combinations thereof.

Certain active chemicals, for example trifluralin, are solid at room temperature and others (e.g. tefluthrin, permethrin) are extremely viscous like grease or molasses. Active chemicals in a solid or highly viscous state are not blendable with a carrier. Accordingly, the active chemicals must be treated in a manner to bring their viscosity to a level that is blendable with the carrier. A preferred method is heating to decrease the viscosity of the active chemical. Heating is preferably from about 5° C. to about 10° C. above the melting point of the active chemical. Alternatively, the active chemical may be mixed with a solvent or mechanically sheared to reduce its viscosity. Other active chemicals (e.g. Endothall) are blendable with the carrier without treatment to reduce their viscosity. Thus, insuring that the active chemical is blendable with the carrier is defined as simply checking the viscosity of the active chemical and only treating to reduce viscosity for blendability with the carrier if necessary. Table 1 identifies several active chemicals and the temperature for heating to bring them to a blendable viscosity.

TABLE 1

| Active Chemical Blendable Viscosity | | |
|---|---|---|
| Active Chemical | Temperature (°C.) | Viscosity |
| Permethrin | 42 | flowable |
| Cyfluthrin | 65 | flowable |
| Lambdacyhalthrin | 55 | flowable |
| Tefluthrin | 51 | flowable |
| Resmethrin | 55 | flowable |
| Deltamethrin | 120 | flowable |
| Trifluralin | 58 | flowable |

The presence of water may lead to flaws in the form of bubbles or voids in thermoset or thermoplastic materials when they are formed. Additionally, moisture on the carrier can inhibit absorption of the active chemical. Accordingly, the carrier is dried to remove any moisture. Drying may be by heating or by exposure to a desiccant.

The active chemical and carrier are blended in sufficient amounts to produce a bound friable mixture. The bound friable mixture is characterized by small granules of carrier powder particles adhering to active chemical similar to concrete or mortar with insufficient water. The ratio by weight of active chemical and carrier to achieve a bound friable mixture will vary depending upon the active chemical and the carrier. Table 2a provides examples of approximate amounts of particular active chemicals and carriers that have been found to provide a bound friable mixture. When high release rates are needed early in product life, a weight ratio of active chemical to carbon black of about 0.5 is used.

For moderate levels of early release and longer longevity a weight ratio of about 2 is used. For longer longevities and slow release of a large reserve of active chemical a ratio of about 4 is used.

TABLE 2a

Bound Friable Mixtures

| Active Chemical (AC) | Carrier (C) | AC/C Wt Ratio |
|---|---|---|
| Tefluthrin | Carbon Black[a] | 0.5–4.0 |
| Lambdacyhalthrin | Carbon Black | 0.5–3.0 |
| permethrin | Carbon Black | 0.5–3.0 |
| Deltamethrin | Carbon Black | 0.5–4.0 |

[a]Carbon Black is Vulcan XC-72

Table 2b provides examples of the ratios by weight of active chemical to polymer absorbable within the polymer with and without a carrier. Comparing columns 3 and 4 of Table 2b, shows that addition of a carrier greatly enhances the amount of active chemical in the controlled release product.

TABLE 2b

Weight Ratio of Active Chemical to Polymer With and Without Carbon Black (CB)

| Active Chemical (AC) | Polymer (P) | AC/P Wt Ratio | AC/P Ratio (5 wt % CB) |
|---|---|---|---|
| Permethrin | LDPE 763[a] | 1.8 | 2.3 |
| Permethrin | Urethane 2200[b] | 0.5 | 0.8 |
| Tefluthrin | LDPE 763 | 1.7 | 2.2 |
| Tefluthrin | Urethane 2200 | 0.3 | 0.6 |

[a]LDPE 763 is a low density polyethylene, specifically Microthene 763-00
[b]Urethane 2200 is BF Goodrich Polyurethane 2200 Type 58134NAT 025D The bound friable mixture is mixed with an amount of dispersable polymer powder making a premixture to achieve about 10 wt % active chemical in the final controlled release product. It is preferred that the dispersable polymer powder be a thermoplastic. The amount of dispersable polymer powder is greater than the amount of the bound friable mixture by weight. Preferred weight ratios of dispersable polymer to bound friable mixture range from about 10 to about 200. The purpose of the premixture is to develop a homogeneous dispersion of bound friable mixture in polymer powder. Although a homogeneous dispersion may be achieved with higher ratios of dispersable polymer powder to bound friable mixture, more mixing time is required, and it is more difficult to avoid lumps.

Upon obtaining a premixture that is substantially homogeneous, additional mixable polymer powder is added to make a formable mixture. The mixable polymer powder may be the same as or different from the dispersable polymer powder. The mixable polymer powder may be of the same or different particle size or of the same or different chemical composition or any combination thereof. It is preferred that the mixable polymer powder be a thermoplastic.

The formable mixture may be formed by any plastic forming process, for example extrusion. It has been found that extrusion of the formable mixture of the present invention results in flaw free controlled release devices. Moreover, the controlled release devices made according to the present invention have a more predictable life. This is because absence of flaws in the form of voids or bubbles reduces the opportunity for the active chemical to freely travel through flaws thereby increasing the life of the controlled release product.

EXAMPLE 1

Several formulations of active chemical, carrier and polymer were made according to the present invention (See Tables E1a and E1b) to determine release rate of active chemical and biological efficacy.

Release rates reported in Tables E1a–E1d were measured after cleaning product surfaces to remove any active material that may have been on the product surfaces after product forming. The carrier used was carbon black, specifically Vulcan XC-72.

Some of the entries in the Tables E1a–E1d have two values for release rate. The first is the "brand new" release rate and the second is the release rate after the controlled release product had been in the field for from 4–6 months. Several of the formulations from Tables E1a–E1d were used for efficacy tests, specifically toxicity studies.

TABLE E1a

Formulation and Release Rate

| Active Chemical | Carrier (Carbon Black) | Polymer | Release Rate $\mu g/cm^2/d$ |
|---|---|---|---|
| Diazinon | | | |
| 10 wt % | 10 wt % | HDPE [a] | 11.7 |
| 10 wt % | 10 wt % | LDPE | 17.6 |
| Chlorpyrifos | | | |
| 10 wt % | 10 wt % | HDPE | 28.1 |
| 10 wt % | 10 wt % | LDPE | 45.3 |
| 6 wt % | 0.5 wt % | Polyester | 1.86 |
| 6 wt % | 0.5 wt % | Polypropylene | 25.6 |

[a] HDPE is a high density polyethylene, specifically Polyethylene MA778000

TABLE E1b

Formulation and Release Rate

| Active Chemical | Carrier (CB) | Polymer | Release Rate |
|---|---|---|---|
| Cyfluthrin | | | |
| 10 wt % | 10 wt % | HDPE | 1.2 |
| 20 wt % | 10 wt % | HDPE | 1.6 |
| 20 wt % | 10 wt % | LDPE 763 | 5.8 |
| 10 wt % | 5 wt % | LDPE 763 | 12 |
| 10 wt % | 10 wt % | LDPE 763 | 27.4 |
| 3 wt % | 0.5 wt % | Hytrel[a] | 2.6 |
| 3 wt % | 0.5 wt % | Polypropylene | 6.1 |
| Resmethrin | | | |
| 10 wt % | 10 wt % | LDPE 763 | 0.39 |
| 10 wt % | 10 wt % | Hytrel | 1.2 |
| 10 wt % | 10 wt % | Urethane 2200 | 0.44 |
| 10 wt % | 10 wt % | LDPE 763 | 0.39 |
| Permethrin | | | |
| 10 wt % | 10 wt % | LDPE 763 | 12 |
| 10 wt % | 10 wt % | Hytrel | 4.4 |
| 10 wt % | 10 wt % | Urethane 2200 | 1.6 |
| 10 wt % | 5 wt % | HDPE | 2.2–1.5 |
| 20 wt % | 10 wt % | LDPE 763 | 37 |
| 5 wt % | 2.5 wt % | Urethane 2200 | 1.9 |

TABLE E1b-continued

Formulation and Release Rate

| Active Chemical | Carrier (CB) | Polymer | Release Rate |
|---|---|---|---|
| 10 wt % | 5 wt % | LDPE 763 | 3.9 |
| 10 wt % | 10 wt % | LDPE 763 | 8.9 |
| 10 wt % | 5 wt % | LDPE 763 | 3.9 |

[a]Hytrel is a polyester

TABLE E1c

Formulation and Release Rate

| Active Chemical | Carrier (Carbon Black) | Polymer | Release Rate $\mu g/cm^2/d$ |
|---|---|---|---|
| Tefluthrin | | | |
| 2 wt % | 1 wt % | HDPE | 0.52 |
| 5 wt % | 0 wt % | HDPE | 1.6 |
| 5 wt % | 2.5 wt % | HDPE | 5.3–2.1 |
| 5 wt % | 5 wt % | HDPE | 1.1 |
| 5 wt % | 10 wt % | HDPE | 0.56 |
| 5 wt % | 20 wt % | HDPE | 2.3 |
| 10 wt % | 0 wt % | HDPE | 1.9 |
| 10 wt % | 5 wt % | HDPE | 5.3–4.4 |
| 10 wt % | 10 wt % | HDPE | 1.4 |
| 10 wt % | 20 wt % | HDPE | 1.2 |
| 10 wt % | 40 wt % | HDPE | 5.5 |
| 10 wt % | 5 wt % | LDPE 763 | 6.9–5.0 |
| 5 wt % | 2.5 wt % | LDPE 763 | 7.0–4.2 |
| 20 wt % | 10 wt % | Urethane 2200 | 18 |
| 5 wt % | 2.5 wt % | Polypropylene | 6.0 |
| 10 wt % | 5 wt % | Polypropylene | 6.9 |

TABLE E1d

Formulation and Release Rate

| Active Chemical | Carrier (Carbon Black) | Polymer | Release Rate $\mu g/cm^2/d$ |
|---|---|---|---|
| Lamdacyhalthrin | | | |
| 2 wt % | 1 wt % | HDPE | 0.8 |
| 5 wt % | 0 wt % | HDPE | 1.3 |
| 5 wt % | 2.5 wt % | HDPE. | 2.0–1.0 |
| 5 wt % | 5 wt % | HDPE | 1.0 |
| 5 wt % | 10 wt % | HDPE | 0.8 |
| 5 wt % | 20 wt % | HDPE | 1.1 |
| 10 wt % | 0 wt % | HDPE | 1.4 |
| 10 wt % | 5 wt % | HDPE | 2.8–1.2 |
| 10 wt % | 10 wt % | HDPE | 1.5 |
| 10 wt % | 20 wt % | HDPE | 2.4 |
| 10 wt % | 40 wt % | HDPE | 2.3 |
| 1 wt % | 0.5 wt % | LDPE 763 | RR < 0.1 |
| 5 wt % | 2.5 wt % | LDPE 763 | 2.9–1.1 |
| 10 wt % | 5 wt % | LDPE 763 | 8.3–8.8 |
| 20 wt % | 10 wt % | LDPE 763 | 12 |
| 1 wt % | 0.5 wt % | Polyurethane | RR < 0.1 |
| 5 wt % | 2.5 wt % | Polyurethane | 4.4 |
| 10 wt % | 5 wt % | Polyurethane | 7.3 |
| 1 wt % | 0.5 wt % | Polyureth/LDPE | 2.6 |
| 5 wt % | 2.5 wt % | Polyureth/LDPE | 5.5 |
| 10 wt % | 5 wt % | Polyureth/LDPE | 8.3 |

FIRE ANTS

Pot liners were made for testing against fire ants. The pot liners contained either chlorpyrifos or cyfluthrin with 0.5 wt % carbon black in either polyester or polypropylene. Pot liners lacking both chlorpyrifos and cyfluthrin were used as controls. Pot liners were supplied to the USDA Imported Fire Ant Station in Gulfport MS in 1992. Pot liners were placed into standard 1 gallon containers with untreated soil media and placed outdoors to age under simulated nursery conditions. Aged pots were then placed within fire ant population areas and monitored monthly for occupation and avoidance behavior. Initially, there was no fire ant occupation of the pots containing chlorpyrifos or cyfluthrin. Occupation occurred in the untreated pots. After 9 months, the pots having 3 wt % active chemical remained unoccupied whereas the other treated pots were occupied. After 16 months, the 3 wt % active pots were still unoccupied.

During part of the study, desiccation was used to force the fire ants to choose between the pots and the desiccated soil. Fire ants initially entered treated pots, then left and died external to the pots, or they moved as far as possible from the pots and died.

FLIES

Contact strips for controlling flies were made with resmethrin and permethrin of 10 wt %, carbon black of 10 wt % and using thermoplastic polyurethane 2200 (Polyu2200), Hytrel thermoplastic polyester polymers (Microthene 763). The average dead fly-count was 7.3 flies per window per week before and after use of the treated strips. The strips were placed in a window and observed for two weeks. The results are shown in TABLE E1e.

TABLE E1e

Dead Fly Count

| Active Chemical | Polymer | Fly Count Flies/window/week |
|---|---|---|
| Resmethrin | Microthene 763 | 18.5 |
| Resmethrin | Hytrel | 23 |
| Permethrin | Urethane 2200 | 30 |
| Permethrin | Microthene 763 | 48 |

Release rates for resmethrin ranged from 0.4–1.2 ug/cm$^2$/day whereas release rates for permethrin ranged from 1.6–12.0 ug/cm$^2$/day which was more effective.

TERMITES

Figure 1A:
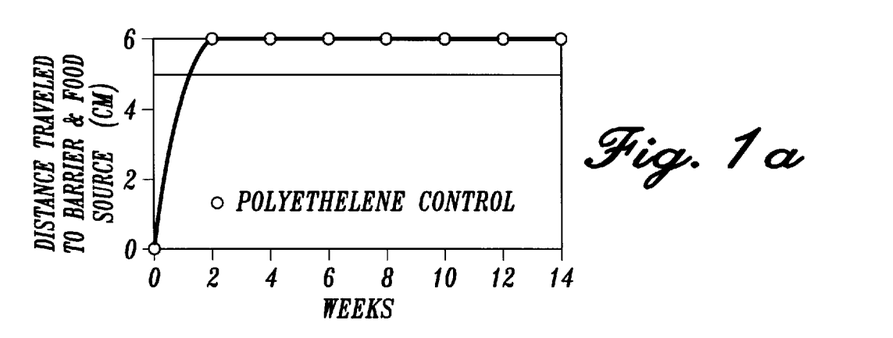
FIG. 1a is a graph of termite penetration versus time for a polyethylene control.
Figure 1B:
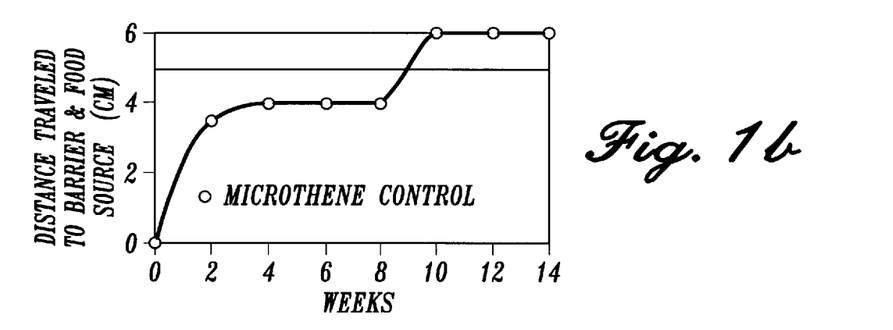
FIG. 1b is a graph of termite penetration versus time for a microthene control.
Figure 1C:
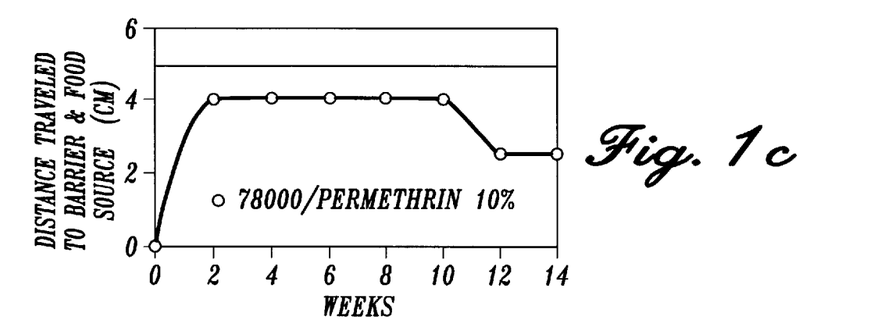
FIG. 1c is a graph of termite penetration versus time for HDPE with permethrin.
Figure 1D:
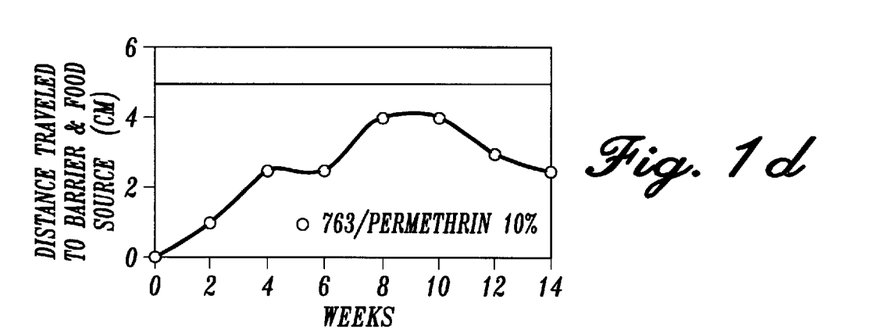
FIG. 1d is a graph of termite penetration versus time for LDPE with permethrin.
Figure 1E:
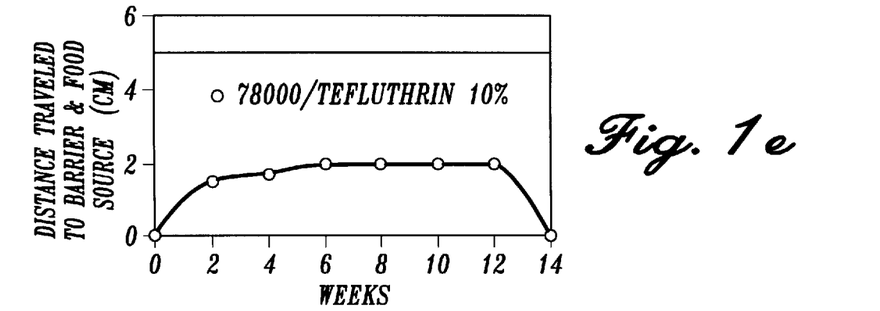
FIG. 1e is a graph of termite penetration versus time for HDPE with tefluthrin.
Figure 1F:
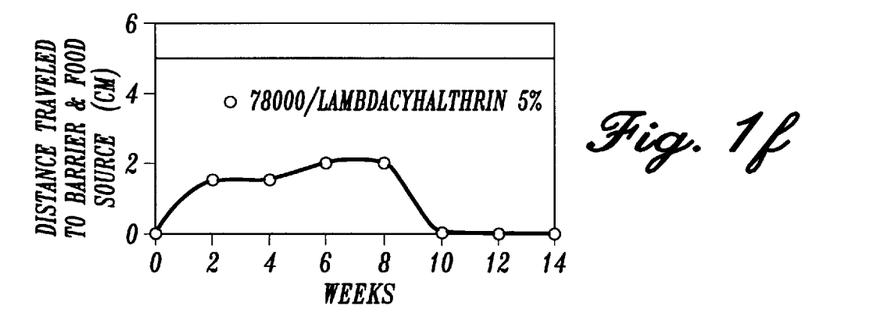
FIG. 1f is a graph of termite penetration versus time for HDPE with 5% lambdacyhalthrin.
Figure 1G:
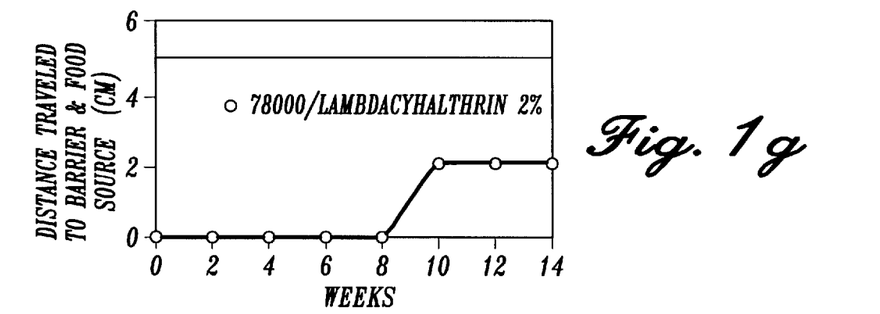
FIG. 1g is a graph of termite penetration versus time for HDPE with 2% lambdacyhalthrin.
Figure 1H:
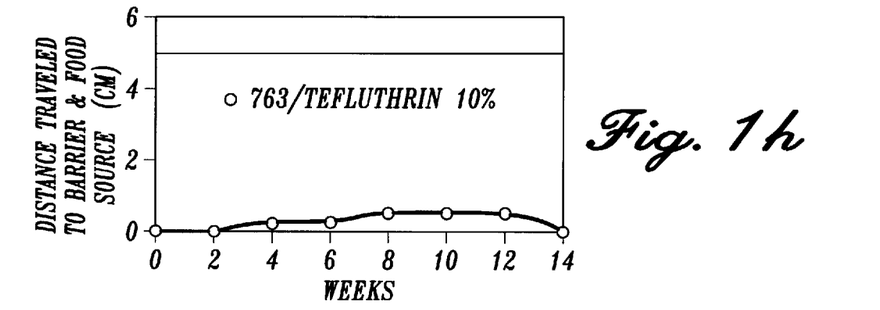
FIG. 1h is a graph of termite penetration versus time for LDPE with tefluthrin.
Figure 1I:
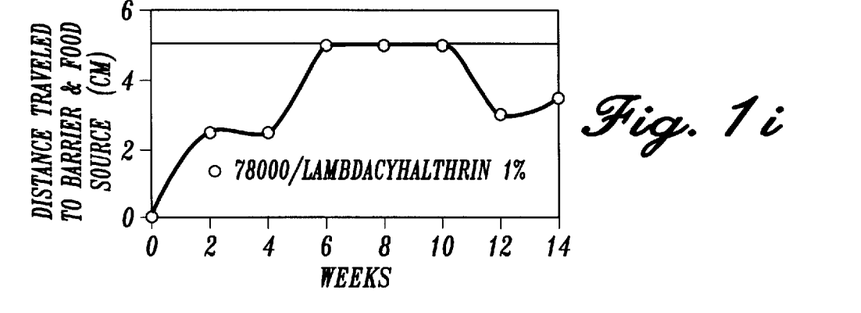
FIG. 1i is a graph of termite penetration versus time for HDPE with 1% lambdacyhalthrin.
Figure 1J:
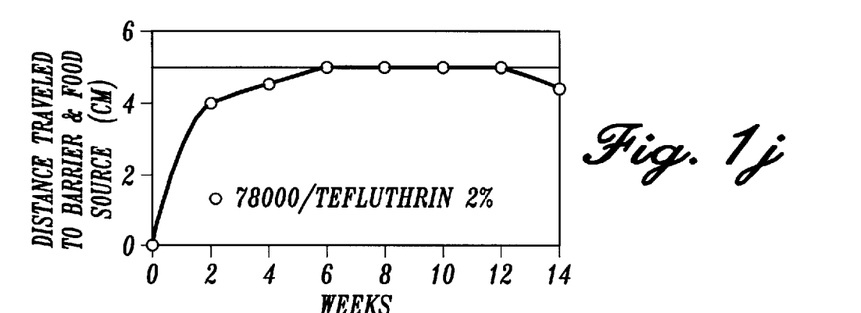
FIG. 1j is a graph of termite penetration versus time for HDPE with 2% tefluthrin.

Controlled release devices were also tested against termites. Active chemicals used were pyrethroids, permethrin, tefluthrin, and lamdacyhalthrin. The ratio of active chemical to carbon black was 2:1 by weight. The polymers used were LDPE (polyethylene 763) and HDPE (polyethylene 78000, Microthene). Test assemblies were made using a tube 10 cm in length. Termites were placed at one end (0.0 cm), a polymer barrier in the center (5.0 cm), and food opposite the termites (6.0 cm). Results are shown in FIGS. 1a–1j. Termite penetration of the control barriers having no active chemical occurred in 2 weeks for LDPE and 10 weeks for HDPE. No penetration occurred through any barrier having an active chemical over a 14 week period. Termite proximity to a barrier having an active chemical varied with the amount of active chemical released from the polymer. An effort was made to reduce release rate to permit the termites to approach the barrier but not penetrate the barrier. FIGS. 1i and 1j are for lamdacyhalthrin 1 wt % in HDPE and tefluthrin 2 wt % in HDPE respectively and demonstrate that no penetration occurred for reduced release rate systems.

For termites, it is preferred to deploy a sheet of controlled release product. Sheets range from about 10 mil to about 60 mil in thickness. Release rates resulting in longevities from about 2 years to over 60 years are achievable and predictable given the polymer, active chemical, carrier, concentrations thereof and operating temperature. For HDPE, tefluthrin, lambdacyhalthrin, permethrin and carbon black with a weight ratio of active chemical to carbon black of 1:1, sheet thickness of 60 mil, 0.05 wt % active chemical, longevity is about 13 years at 23° C. and about 45 years at 15° C. By increasing carbon black to 1:2, longevity is increased to about 60 years at 15° C. If the sheet is deployed beneath the ground surface, then longevity increases because the soil adjacent the sheet holds the released active chemical thereby decreasing the concentration gradient at the sheet surface that can result in longevity as high as from 77–85 years at 15° C.

Decreasing sheet thickness by half reduces longevity by about half. Decreasing thickness from 60 mil to 10 mil reduces longevity by about a factor of 7.

Increasing active chemical concentration to 0.1 wt % increases longevity by about 50%.

SECOND ASPECT

The problem to be addressed by the second aspect of the present invention is to achieve near 100% pest lethality while avoiding toxcicity to humans. This problem statement translates to a product having a surface concentration of an active chemical from about 2 ug/cm$^2$ to about 15 ug$^2$/cm Further, it is desired that the controlled release product have a functional longevity from about 6 months to about 12 months.

According to a second aspect of the present invention, a microsponge of polymer holds active chemical permitting the active chemical to wet the surface of the microsponge without dripping from or crystallizing on the surface so that as an insect contacts the surface, active chemical is removed from the surface onto the insect. The active chemical from within the microsponge replenishes the locations on the surface where active chemical has been removed. The microsponge polymer has a formulation that would lead to a medium hardness (durometer) from about 60A to about 55D. However, the microsponge is not abrasion resistant so that even the clawed appendages of a cockroach are able to leave delible marks in the surface of the microsponge.

The microsponge is achieved by a method of making a controlled release device having a polymer and an active chemical having the steps of:

(a) selecting an amine curable elastomer pre-polymer;

(b) heating the pre-polymer making a first solution;

(c) heating and mixing a trialkanolamine with a soft segment cross-linker making a second solution;

(d) mixing the active chemical into either the first solution, second solution or both; and (e) pouring said second solution together with said first solution into a combined solution and continuing heating while mixing said combined solution into a castable mixture; and (e) casting said castable mixture.

In a preferred embodiment, the active chemical is mixed into the first solution. An alternative embodiment is to mix the active chemical with the soft segment cross-linker then mix with the trialkanolamine for the second solution and the first solution has only amine curable pre-polymer.

Amine curable elastomer pre-polymers include casting urethanes and other thermoset elastomers. Casting urethanes are thermoset plastics including but not limited to solithane, and combinations thereof. Thermoset elastomers include but are not limited to polyisoprene (a vulcanized crosslinked rubber), a blend of epoxy resin with carboxylated latex (Shell Hycar), and combinations thereof.

A carrier is not needed for castable pre-polymers, specifically casting urethanes, thermoset urethanes, and liquid crystal polyesters because these polymers have a combination of hard segments and soft segments that creates free volume structures within the polymers referred to herein as microsponge. These structures can act as reservoirs for the active ingredients without the need for carriers.

The active chemical is first mixed with the pre-polymer to obtain a substantially homogeneous first mixture or first solution of active chemical in the pre-polymer. It is preferred to avoid mixing active chemical into soft segment cross linker because when the soft segment cross linker and pre-polymer are mixed, there may be insufficient time to obtain a substantially homogeneous mix before substantial cross linking has occurred.

It was found that using low trialkanolamine, specifically triisopropanolamine (TIPA), typically done in making cast urethanes, resulted in excessively high release rates of active chemical from the cast urethane permitting formation of crystals of active chemical on the surface of the cast urethane. It was discovered that by combining a soft segment cross linker with a high amount of trialkanolamine that adequate release rates were obtained without formation of crystals.

If the active chemical has functional groups that react with the amine curable pre-polymer, (eg hydroxyl group(s), amine(s)), mixing the active chemical with the amine curable pre-polymer in the first solution will expose the active chemical to the amine curable pre-polymer and may react with it thereby destroying or diminishing active chemical molecules and possibly also reducing polymerization of the final product. Accordingly, for active chemicals with functional groups reactive with amine curable pre-polymer, it is preferred that the active chemical be first mixed with the amine (eg trialkanolamine) and soft segment cross linker (eg C113) in the first solution. Then, when the amine curable pre-polymer (eg isocyanate) is added, the amine curable pre-polymer it tends to react first with the soft segment cross linker thereby reducing the amount of unwanted reaction with the active chemical.

EXAMPLE 2

Several formulations were made and release rates measured, Results are shown in TABLE E2a, and TABLE E2b. The Krayton and Polyisoprene were made simply by adding the active chemical (cyfluthrin) to a standard thermoset formulation.

The reduced release rate is beneficial to longer life controlled release product.

TABLE E2a

Formulation and Initial Release Rate for
Selected Elastomer Based Controlled Release Products

| Active Chemical | Elastomer | Type | Initial Release Rate µg/cm$^2$/d |
|---|---|---|---|
| cyfluthrin | | | |
| 33 wt % | Kraton D1101 | Thermoplastic | 91 |
| 33 wt % | Polyisoprene | Crosslinked Rubber | 54 |
| 33 wt % | Hycar[a] | Blend | 7 |

[a]Hycar is Shell epoxy 828/Hycar

TABLE E2b

Formulation and Release Rate

| Active Chemical | Thermoset | Release Rate $\mu g/cm^2/d$ |
|---|---|---|
| deltamethrin | | |
| 15 wt % | Aromatic 80 A | 4.4 |
| 15 wt % | Pellethane 2102 80 A | 4.6 |
| 15 wt % | Pellethane 2012 55D | 5.4 |
| 15 wt % | Pellethane 2101 55D + 5 wt % carbon black | 2 |
| 15 wt % | Aliphatic PS-49-100 | 5.6 |

Note that a carrier (carbon black) may be used to reduce release rate compared to no carrier.

CONTROLLED RELEASE COMPOSITION

According to a further aspect of the present invention, a controlled release composition having a urethane containing an active chemical may be an improved composition having
(a) the urethane is a casting urethane having ur linkages;
(b) a soft segment cross-linker; and
(c) a trialkanolamine cross-linker/catalyst in an amount from about 1.0 wt % to about 5 wt %.

The casting urethane is preferably in an amount of at least 54 wt %. The soft segment cross linker is preferably in an amount up to about 26 wt %.

The active chemical is in an amount from about 0.5 wt % to about 33 wt %.

Ur linkages include urethane linkages, urea linkages, or both.

CLOSURE

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. A method of making a controlled release device, said controlled release device having a polymer, a carrier, and an active chemical, the method vaporizing said active chemical, wherein the improvement comprises the steps of:
   (a) insuring that the active chemical is blendable with the carrier;
   (b) removing moisture from the carrier;
   (c) blending said active chemical with the dried carrier into a bound friable mixture;
   (d) adding the bound friable mixture into an amount of a polymer preform and forming a formable mixture;
   (e) forming the formable mixture into the controlled release device with substantially reduced vaporization.

2. The method as recited in claim 1, wherein said polymer preform is a polymer powder.

3. The method as recited in claim 2, wherein adding comprises the steps of:
   (i) dispersing the bound friable mixture into an amount of said polymer powder wherein the amount of the polymer powder is greater than the amount of bound friable mixture by weight thereby making a premixture; and
   (ii) mixing the premixture with an additional amount of said polymer powder, wherein the amount of the said additional amount is greater than the amount of the premixture by weight thereby making said formable mixture.

4. The method as recited in claim 1, wherein the step of insuring comprises heating said active chemical and reducing its viscosity.

5. The method as recited in claim 1, wherein the step of removing moisture comprises heating said carrier.

6. The method as recited in claim 1, wherein said active chemical is a pyrethroid.

7. The method as recited in claim 1, wherein said polymer is a thermoplastic or a thermoset.

8. The method as recited in claim 7, wherein said thermoplastic is selected from the group consisting of polyethylene, polyester, polyurethane, polypropylene, urethane, styrene block copolymer, pellethane and combinations thereof.

9. The method as recited in claim 7, wherein said thermoset is selected from the group consisting of casting urethanes, polyolefins, epoxies, aromatics and combinations thereof.

10. The method as recited in claim 6, wherein said pyrethroid is selected from the group consisting of resmethrin and permethrin.

11. The method as recited in claim 1, wherein said carrier is carbon black.

12. The method as recited in claim 1, wherein said carrier is present up to about 40 wt %.

13. The method as recited in claim 12, wherein said carrier is present up to about 10 wt %.

14. The method as recited in claim 13, wherein said carrier is present up to about 5 wt %.

15. The method as recited in claim 1, wherein said active chemical is present up to about 33 wt %.

16. The method as recited in claim 15, wherein said active chemical is present up to about 20 wt %.

17. The method as recited in claim 16, wherein said active chemical is present in an amount less than or equal to about 10 wt %.

18. The method as recited in claim 1, wherein said active chemical and said carrier are present in a weight ratio of about 2:1.

19. The method as recited in claim 1, wherein said polymer preform is a pre-polymer.

20. The method as recited in claim 19, wherein adding comprises the steps of:
   (i) selecting said pre-polymer is an amine curable elastomer pre-polymer;
   (ii) heating the elastomer pre-polymer making a first solution;
   (iii) heating and mixing an amine with a soft segment cross-linker making a second solution;
   (iv) mixing the bound friable mixture with either the first solution, second solution or both; and
   (iv) pouring said second solution together with said first solution into a combined solution and continuing heating while mixing said combined solution into said formable mixture.

21. The method as recited in claim 19, wherein said forming is casting.

22. The method as recited in claim 20, wherein said pre-polymer is solithane.

23. The method as recited in claim 20, wherein said amine is an alkanolamine.

24. The method as recited in claim 20, wherein said alkanolamine is present in an amount greater than 0.2 wt %.

25. A method of making a controlled release device having a polymer and an active chemical, the method comprising the steps of:

(a) selecting an amine curable elastomer pre-polymer;

(b) heating the pre-polymer making a first solution;

(c) heating and mixing an amine with a soft segment cross-linker making a second solution;

(d) mixing the active chemical into either the first solution, second solution or both;

(d) pouring said second solution together with said first solution into a combined solution and continuing heating while mixing said combined solution into a castable mixture; and (e) casting said castable mixture.

26. The method as recited in claim 25, wherein said pre-polymer is selected from the group consisting of solithane, pellethane, polyisoprene, epoxy resin, carboxylated latex, and combinations thereof.

27. The method as recited in claim 25, wherein said amine is an alkanolamine.

28. The method as recited in claim 27, wherein said alkanolamine is trialkanolamine.

29. The method as recited in claim 28, wherein said trialkanolamine is present in an amount greater than 0.2 wt %.

30. The method as recited in claim 25, further comprising mixing a carrier into the first solution.

31. The method as recited in claim 30, wherein said carrier is carbon black.

32. The method as recited in claim 25, wherein said pouring comprises the step of:

pouring said first solution into said second solution.

33. The method as recited in claim 25, wherein said active chemical has at least one functional group reactive with said amine curable elastomer pre-polymer.

34. The method as recited in claim 33, wherein said second solution contains the amine, the soft segment cross linker and said active chemical.

35. The method as recited in claim 34, wherein said pouring comprises pouring the first solution containing no active chemical into said second solution.

36. A microsponge made by the method of claim 25.

37. A controlled release composition comprising a urethane containing an active chemical, wherein the improvement comprises:

(a) said urethane is a casting urethane having ur linkages;

(b) a soft segment cross-linker; and (c) a trialkanolamine cross-linker/catalyst in an amount from about 1.0 wt % to about 5 wt %.

38. The composition as recited in claim 37, wherein said casting urethane is in an amount of at least 54 wt %.

39. The composition as recited in claim 37, wherein said soft segment cross linker is in an amount up to about 26 wt %.

40. The composition as recited in claim 37, wherein said active chemical is in an amount from about 0.5 wt % to about 33 wt %.

41. The composition as recited in claim 37, further comprising a carrier.

42. The composition as recited in claim 41, wherein said carrier is selected from the group consisting of carbon black, activated carbon, graphite, alumina, silico alumina, and combinations thereof.

43. The composition as recited in claim 41, wherein said carrier is in an amount of at least 5 wt %.

44. A method of making a controlled release device, said controlled release device having a polymer, a dry solid carrier, and a liquid active chemical, the method comprising the steps of:

(a) blending said liquid active chemical with the dry solid carrier, forming an active chemical containing carrier;

(b) mixing the active chemical containing carrier with a polymer making a formable mixture;

(c) forming the formable mixture into the controlled release device with substantially reduced release rate.

45. The method as recited in claim 44, wherein said mixing comprises the steps of:

(i) dispersing the active chemical containing carrier into an amount of said polymer powder wherein the amount of the polymer powder is greater than the amount of the active chemical containing carrier by weight thereby making a premixture; and (ii) mixing the premixture with an additional amount of said polymer powder, wherein the amount of the said additional amount is greater than the amount of the premixture by weight thereby making the formable mixture.

46. The method as recited in claim 44, further comprising the step of:

heating said active chemical to liquefy it and to reduce its viscosity.

47. The method as recited in claim 44, further comprising the step of:

removing moisture by heating said carrier prior to said blending.

* * * * *